United States Patent
Rziha et al.

(10) Patent No.: US 11,286,500 B2
(45) Date of Patent: Mar. 29, 2022

(54) RECOMBINANT ORF VIRUS VECTOR

(71) Applicant: Eberhard Karls Universität Tübingen Medizinische Fakultät, Tübingen (DE)

(72) Inventors: Hanns-Joachim Rziha, Tübingen (DE); Ralf Amann, Tübingen (DE)

(73) Assignee: EBERHARD KARLS UNIVERSITÄT TÜBINGEN MEDIZINISCHE FAKULTÄT, Tubingen (DE)

( * ) Notice: Subject to any disclaimer, the term of this patent is extended or adjusted under 35 U.S.C. 154(b) by 974 days.

(21) Appl. No.: 15/875,389

(22) Filed: Jan. 19, 2018

(65) Prior Publication Data

US 2018/0148739 A1 May 31, 2018

Related U.S. Application Data

(63) Continuation of application No. PCT/EP2016/066926, filed on Jul. 15, 2016.

(30) Foreign Application Priority Data

Jul. 20, 2015 (DE) ..................... 10 2015 111 756.8

(51) Int. Cl.
  *C12N 15/86* (2006.01)
  *A61K 39/00* (2006.01)
  *C12N 15/85* (2006.01)

(52) U.S. Cl.
  CPC .............. *C12N 15/86* (2013.01); *A61K 39/00* (2013.01); *A61K 2039/5154* (2013.01); *C12N 2015/8572* (2013.01); *C12N 2015/8581* (2013.01); *C12N 2710/24031* (2013.01); *C12N 2710/24041* (2013.01); *C12N 2710/24222* (2013.01); *C12N 2710/24243* (2013.01); *C12N 2840/10* (2013.01)

(58) Field of Classification Search
  CPC .............................. C12N 15/86; C12N 15/863
  See application file for complete search history.

(56) References Cited

U.S. PATENT DOCUMENTS

| | | | | |
|---|---|---|---|---|
| 6,365,393 | B1 * | 4/2002 | Schmeer ................ | A61P 37/02 435/235.1 |
| 2013/0108704 | A1 | 5/2013 | Weber et al. | |

FOREIGN PATENT DOCUMENTS

| | | |
|---|---|---|
| CN | 1217751 A | 5/1999 |
| CN | 1443076 A | 9/2003 |
| CN | 101035906 A | 9/2007 |
| CN | 102858966 A | 1/2013 |
| CN | 103079593 A | 5/2013 |
| JP | 2000-507092 A | 6/2000 |
| KR | 10-2007-0055860 | 1/2008 |
| KR | 10-2010-0003490 | 10/2010 |
| WO | WO 97/32029 A1 | 9/1997 |
| WO | WO 2013/172721 A1 | 11/2013 |

OTHER PUBLICATIONS

First Examination Report in corresponding New Zealand Application No. 739286, dated Oct. 18, 2018.
Marsland, B.J. et al. 2003 "Construction of a recombinant orf virus that expresses an *Echinococcus granulosus* vaccine antigen from a novel genomic insertion site" *Arch Virol* 148: 555-562.
Mcinnes, C.J. et al. 2005 "Glycosylation, Disulfide Bond Formation, and the Presence of a WSXWS-Like Motif in the Orf Virus GIF Protein Are Critical for Maintaining the Integrity of Binding to Ovine Granulocyte-Macrophage Colony-Stimulating Factor and Interleukin-2" *Journal of Virology* 79: 11205-11213.
Spehner, D. et al. 2004 "Appearance of the Bona Fide Spiral Tubule of Orf Virus Is Dependent on an Intact 10-Kilodalton Viral Protein" *Journal of Virology* 78: 8085-8093.
Amann et al. 2013 "A new rabies vaccine based on a recombinant Orf Virus (Parapoxvirus) expressing the rabies virus glycoprotein" *J Virol* 87: 1618-1630.
Buttner and Rziha 2002 "Parapoxviruses: From the Lesion to the Viral Genome" *J Vet Med* B 49: 7-16.
Fischer et al. 2003 "Novel Recombinant Parapoxvirus Vectors Induce Protective Humoral and Cellular Immunity against Lethal Herpesvirus Challenge Infection in Mice" *J Virol* 77: 9312-9323.
Li et al. 2015 "Comparative genomic sequence analysis of Chinese orf virus strain NA1/11 with other parapoxviruses" *Archives of Virology* 160: 253-266.
Ning et al. 2011 "Generation of recombinant Orf virus using an enhanced green fluorescent protein reporter gene as a selectable marker" *BMC Veterinary Research* 7: 80 (in 11 pages).
Rohde et al. 2013 "New Orf Virus (Parapoxvirus) Recombinant Expressing H5 Hemagglutinin Protects Mice against H5N1 and H1N1 Influenza A Virus" *PLOS One* 8(12): in 13 pages.
Tan et al. 2012 "Development of orf virus as a bifunctional recombinant Vaccine: Surface display of *Echinococcus granulosus* antigen EG95 by fusion to membrane structural proteins" *Vaccine* 30: 398-406.
Decision of Rejection, in corresponding Japanese application JP 2018-522854, dated Feb. 4, 2020.
GenBank Accession AG000488 [online], Feb. 16, 2005, [retrieved on Jan. 23, 2020], URL, https://www.ncbi.nlm.nih.gov/nuccore/AG000488.1.
GenBank Accession AK137921 [online], Oct. 6, 2010, [retrieved on Jan. 23, 2020], URL, https://www.ncbi.nlm.nih.gov/nuccore/AK137921.
Notice of Preliminary Rejection (English Translation) in Korean Patent Application No. 10-2018-7004903, dated Nov. 27, 2019 (10 pages).
Rziha, Hanns-Joachim, et al., "Genomic Characterization of Orf Virus Strain D1701-V (Parapoxvirus) and Development of Novel Sites for Multiple Transgene Expression" Viruses 2019, 11: 127 (in 26 pages).

(Continued)

*Primary Examiner* — Antonio Galisteo Gonzalez
(74) *Attorney, Agent, or Firm* — Knobbe, Martens, Olson & Bear, LLP

(57) ABSTRACT

A nucleic acid molecule can code for an Orf virus vector promoter. A recombinant Orf virus vector can be included in a cell. The nucleic acid molecule, the vector and/or the cell can be included in a composition. The recombinant Orf virus vector can be used for the production of a foreign gene.

19 Claims, 4 Drawing Sheets

Specification includes a Sequence Listing.

(56) References Cited

OTHER PUBLICATIONS

Amann, R. 2014 PhD. Dissertation entitled: "Orf virus vector: development of new selection strategies, identification of new foreign genes Place of insertion as well as production, characterization and efficacy of a recombinant rabies vaccine" The Faculty of Mathematics and Natural Sciences of the Eberhard Karls University of Tubingen (in 76 pages).
Broyles, S.S. 2003 "Vaccinia virus transcription" *J Gen Virol* 84: 2293-2303.
Cottone, R. et al. 1998 "Analysis of genomic rearrangement and subsequent gene deletion of the attenuated Orf virus strain D1701" *Virus Research* 56: 53-67.
Davison, A. J. and Moss, B. 1989 "Structure of Vaccinia Virus Early Promoters" *J Mol Biol* 210: 749-769.
Henkel, M. Ph.D. 207 Dissertation entitled "Parapox virus Orf virus D1701: Attenuation and production of a vector vaccine against Borna's disease" The Eberhard Karls University Tubingen (in 271 pages).
Rziha, H.-J. et al. 2000 "Generation of recombinant parapoxviruses: non-essential genes suitable for insertion and expression of foreign genes" *J Biotechnology* 83: 137-145.
Yang, Z. et al. 2011 "Genome-wide analysis of the 5' and 3' ends of Vaccinia Virus early mRNAs delineates regulatory sequences of annotated and anomalous transcripts" *J Viol* 85:5897-5909.
Israeli Office Action in IL 257025 dated Feb. 3, 2021.
Search Report in Chinese Patent Application No. 201680053548.X dated Jan. 26, 2021.
Notification of First Office Action in Chinese Patent Application No. 201680053548.X dated Feb. 3, 2021.
Written Opinion in Brazilian Patent Application No. BR112018001121 dated Mar. 9, 2021.
Zhu Ai-Hua et al., Construction and Selection of Strong Promoter for Fowlpox Virus Vector, Chinese Journal of Virology, vol. 16, Issue 4, Dec. 31, 2000, pp. 347-351.

* cited by examiner

RECOMBINANT ORF VIRUS VECTOR

CROSS-REFERENCES TO RELATED APPLICATIONS

This application is a continuation of international patent application PCT/EP2016/066926 filed on 15 Jul. 2016 and designating the U.S., which has been published in German and claims priority from German patent application DE 10 2015 111 756.8 filed on 20 Jul. 2015. The entire contents of these prior applications are incorporated herein by reference.

REFERENCE TO SEQUENCE LISTING

This application incorporates by reference the sequence listing submitted as ASCII text filed via EFS-Web on Nov. 10, 2021. The Sequence Listing is provided as a file entitled "54550436_1.txt," created on Nov. 10, 2021, and which is approximately 1,499 bites in size.

FIELD

The present invention relates to a recombinant Orf virus vector, a cell containing the recombinant Orf virus vector, a composition containing the recombinant Orf virus vector according to the invention and/or the cell according to the invention, the use of the recombinant Orf virus vector according to the invention for the expression of a foreign gene and a nucleic acid molecule encoding an Orf virus vector promoter.

BACKGROUND

Viral vectors are used in the biotechnology to introduce genetic material into target cells. The introduced genetic material often encodes foreign genes which serve for the production of a recombinant protein. For this reason viral vectors are a significant platform technology, in particular for the production of recombinant vaccines which are increasingly used, along with the traditional prevention of infectious diseases, also for the development of new, innovative therapeutic concepts, such as e.g. the therapeutic tumor immunization.

The Orf virus (ORFV) belongs to the family of pox viruses and has a variety of characteristics which makes it interesting for the production of recombinant vaccines and prefers it over other technologies. It is the prototype of the genus of the parapox viruses and belongs to the family of the Poxviridae. ORFV are enveloped, complex dsDNA viruses having a morphology that reminds of a ball of wool and have an average size of approx. 260×160 nm. They have a linear DNA genome with high GC content and a size of approx. 130 to 150 kbp, the central region of which is delimited on both sides by ITR regions ("inverted terminal repeats") and ends in a hair-pin structure, which covalently links both DNA single strands to each other. In the central region of the genome there are predominantly genes which are mainly essential for the viral replication and morphogenesis and which are highly conserved among the pox viruses. In contrast, in the ITR regions there are so-called non-conserved virulence genes which significantly determine the host range, the pathogenicity and the immunomodulation and, therefore, characterize the virus.

In pox viruses the viral replication is restricted to the cytoplasm and starts with the binding of the virus to the surface of the host cell. After the fusion the so-called viral core, a protein core is released into the cytoplasm, which contains the viral genome, early viral mRNA and viral transcription factors (TF). In the following the early viral gene expression starts where, under the control of pox-virus specific early promoters, viral mRNA is synthesized. After the disintegration of the core structure the viral DNA is released into the cytoplasm. In contrast to the transcription of "early" genes which exclusively takes place under the control of viral TF the following "intermediate" and "late" gene transcription depends on the assistance of cellular TF. As the consequence, in contrast to the expression of "intermediate" and "late" genes the expression of early genes in pox viruses does neither require the replication of viral DNA nor a virus production.

The ORFV is characterized by a very narrow natural host range which includes sheep and goat. Infections occur via lesions of the skin which allow the penetration of the virus. The replication of the dermatropic virus in the following is restricted to regenerative keratinocytes, which initiates a contagious dermatitis or Ecthyma contagiosum. This usually mildly progressing self limiting infection manifests as locally restricted skin or mucosa lesion, whereby the formation of pustules caused by the massive infiltration of polymorphous nuclear granulocytes mainly appears at the mouth and udder. The lesion heals after approx. 4 to 6 weeks without the formation of scars. A long-lasting immune protection does not develop despite the strong immune response so that a reinfection is possible even after few weeks, although clinical symptoms and the virus production are significantly reduced. A systemic spread or viremia has not been observed for ORFV; also not after experimental intravenous injection of high doses of infectious viruses.

ORFV is considered as zoonotic pathogen and in rare cases can also be passed to humans via the injured skin. After the infection locally restricted modular swellings can be observed which are mostly limited to the fingers and hands, and occasionally there are swellings of the lymph nodes and fever. Normally, the progression is harmless, without complications and heals completely within three to eight weeks without clinical aftermaths. In immunocompromised patients also more severe progressions of the infection have been observed, which, however, after the treatment with antivirals, such as Cidofovir or Imiquimod, have completely healed.

ORFV is interesting for the production of recombinant vaccines. In comparison to orthopox viruses ORFV is characterized by a very narrow natural host tropism which includes sheep and goat. As a consequence, an inhibiting "preimmunity" against the vector in humans, which is caused by a natural infection, as it can be observed in the most common viral vectors of the vaccinia and adenoviruses, can be almost excluded. Furthermore, the exceptionally weak and short-lived ORFV specific vector immunity allows a very effective booster and/or refreshing vaccination or immunization with ORFV based vaccines which are directed against further pathogens.

The administration of ORFV in permissive but also in non-permissive hosts results in a strong immune stimulating reaction which is characterized by a pronounced induction of innate immune mechanisms and the release of interferones, cytokines, and chemokines. Shortly after the immunization dendritic cells accumulate at the injection site and in the following, via the activation of T and B cells, induce a specific adaptive immune response. In contrast to vaccines from inactivated viruses and living vectors which mostly induce a humoral emphasized immune response, the balanced induction of the cellular and the humoral immune response after the immunization with recombinant ORFV is a significant advantage. At the same time it renders the use of adjuvants redundant which may cause unintended side effects and inflammation reactions. Other advantages are, in addition, the possibility of the standardized production of the recombinant vaccines in permanent cell lines without the use of antibiotics and the waiver of a production in hen's egg (increasing number in protein and antibiotics intolerances).

An attenuated ORFV vaccine which is approved in the veterinary field has the designation D1701, in correspondence with the identical ORFV strain. This vaccine which is in inactivated form known under the trade name Baypamun (Bayer) or Zylexis (Pfizer) was initially obtained via the isolation of a wild type virus from sheep and a subsequent adaptation as a result of multiple passaging in bovine kidney culture cells. It was followed by a further adaption in Vero cells (African green monkey kidney cells) which led to the obtainment of the ORFV vector D1701-V. D1701-V is further attenuated and only results in asymptotic infections even in immunosuppressed sheep.

The recombinant ORFV vectors so far use the VEGF locus as the insertion point. According to the present knowledge this results in the supposed advantage that by the elimination of the vegf-e gene which is under the control of a poxvirus-specific "early" promoters and which is considered as a virulence factor a further attenuation of the vector takes place. In the meantime several ORFV based recombinant vaccines were produced and examined in the animal model. Currently recombinant ORFV vaccines are used against various infectious diseases such as for example against the Aujeszky's disease, rabies, Borna disease, influenza or the classical swine fever.

The good immune stimulating and prophylactically usable effect of recombinant Orf viruses could be demonstrated in the last years by establishing a number of vaccines against different viral infectious diseases. An overview on the use of recombinant pox viruses, including ORFV, for the production of recombinant proteins can be found in Rziha et al. (2000), Generation of recombinant parapoxviruses: non-essential genes suitable for insertion and expression of foreign genes, Journal or Biotechnology Vol. 83, pages 137-145, and Buttner and Rziha (2002), Parapoxviruses: From the Lesion to the Viral Genome, J. Vet. Med. B. Vol. 49, pages 7-16.

The restricted use of the current recombinant ORFV vectors can be explained in particular by the long lasting selection proceedings. Especially a production of polyvalent vaccines was so far not possible. Furthermore, the known recombinant ORFV vectors do not have a precisely controllable expression of the foreign genes.

SUMMARY

Against this background it is a problem underlying the invention to provide a new recombinant ORFV vector by means of which the disadvantages of the known ORFV vectors and vector systems can be reduced or avoided.

This problem is solved by the provision of a recombinant Orf virus (ORFV) vector which comprises the following:

(1) at least one nucleotide sequence encoding and expressing a foreign gene, and (2) at least one promoter which controls the expression of the nucleotide sequence, wherein the nucleotide sequence is inserted into at least one of the insertion loci (IL) 1, 2 and 3 which are located in the ORFV genome in the following regions:

|  | IL 1 | IL 2 | IL 3 |
| --- | --- | --- | --- |
| Restriction fragment | HindIII fragment C, KpnI fragment G, BamHI fragment C/G, EcoRI fragment B | HindIII fragment I/J, KpnI fragment B, BamHI fragment A, EcoRI fragment A/E | HindIII fragment G/D, KpnI fragment B, BamHI fragment A, EcoRI fragment D |
| and/or Gene/ORF | 006, 007 (dUTPase), 008 (G1L-Ank), 009 (G2L) | 102, 103 | 114, 115, 116, 117 (GIF) |
| and/or Nucleotid position | nt 500 ± 100 to nt 2,400 ± 600 | nt 5,210 ± 100 to nt 7,730 ± 100 | nt 15,660 ± 100 to nt 17,850 ± 100 |

According to the invention Orf virus (ORFV) refers to all viruses and virus strains falling under the species of *Parapoxvirus ovis*, in particular the strain D1701.

According to the invention a recombinant ORFV vector refers to a vector based on the ORFV genome which is configured for the transport and/or the expression of a foreign gene in(to) biological cells.

According to the invention a foreign gene refers to a gene or open reading frame (ORF) which does not originate from the ORFV genome.

According to the invention a promoter refers to such a nucleic acid section which allows the regulated expression of the foreign gene in the ORFV vector of the invention. Preferably it refers to an ORF promoter, i.e. a promoter existing in the wild type ORFV genome or a promoter derived therefrom, or an artificial promoter, such as a poxvirus promoter, CMV promoter etc.

In the recombinant ORFV vector the position of the insertion loci IL 1, 2 and 3 in the ORFV genome can be determined according to the invention in several ways: by means of restriction fragments, the ORFV genes or open reading frames (ORF) or nucleotide positions in the ORFV genome.

The traditional description of the localization of IL 1, 2 and 3 takes place by means of restriction maps and by means of restriction fragments where the insertion regions are located. The restriction map of the ORFV is exemplarily shown for the strain D1701 in Cottone et al. (1998), Analysis of genomic rearrangement and subsequent gene deletion of the attenuated Orf virus strain D1701, Virus Research, Vol. 56, pages 53-67. The content of this publication is a component of the present disclosure. Here, according to the invention e.g. regarding IL 1 the indications HindIII fragment C, KpnI fragment G, BamHI fragment CIG, EcoRI fragment B mean that this insertion locus extends from the HindIII fragment C up to the EcoRI fragment B. IL 2 extends from the HindIII fragment I-J up to the EcoRI-fragment A/E. IL 3 extends from the HindIII fragment G/D up to the EcoRI fragment D.

The indications 006, 007 (dUTPase), 008 (G1 Li-Ank), 009 (G2L) for IL 1 mean that the insertion locus extends from gene or ORF 006 up to gene or ORF 009. The indications in the brackets refer to the coding products or encoded enzymatic activities insofar they are currently known.

According to the invention IL 1 is located in a region which starts at nucleotide 400 to 600 (500±100) and ends at nucleotide 1800 to 3000 (2,400±600).

What has been said for IL 1 applies to IL 2 and IL 3 in accordance with the above table.

The indicated positions of the nucleotides (nt) were established by the inventors from multiple determinations in different ORFV strains. The examinations for the strain D1701 or variants therefrom resulted in the following positions which are especially preferred:
IL 1: nt 496-nt 2,750; nt 496-nt 1,912 and nt 511-2,750
IL 2: nt 5,212-7,736
IL 3: nt 15,656-17,849.

The inventors have realized that into the indicated newly found insertion loci foreign genes can be stably integrated into the ORFV genome. This was surprising. So far it was assumed that the regions of the insertion loci in the genome are required for the virus replication and were inappropriate for the expression of foreign genes.

It has turned out being a significant advantage of the ORFV vector according to the invention that by the choice of the insertion locus the gene expression can be controlled. For example, the expression of foreign genes in IL 2 is decreased over the expression in the so far used VEGF locus by the factor 2. Furthermore, by the choice of the promoter the strength and the point in time of the expression of the foreign gene can be influenced in a targeted manner.

The problem underlying the invention is herewith completely solved.

In an embodiment of the recombinant ORFV vector which is preferred according to the invention ORFV is of the strain D1701.

This measure has the advantage that such a vector is used which is attenuated and only causes asymptotic infections in the host. According to the invention all variants of D1701 are covered, including D1701-B and D1701-V.

According to a further embodiment of the recombinant ORFV vector which is preferred according to the invention the promoter is an ORFV promoter, further preferably an early ORFV promoter, which preferably comprises a nucleotide sequence which is selected from: SEQ ID No. 1 (P1 promoter), SEQ ID No. 2 (P2 promoter), SEQ ID No. 3 (optimized "early" promoter), SEQ ID No. 4 (7.5 kDa promoter), and SEQ ID No. 5 (consensus "early" promoter).

This measure has the advantage that such promoters are used which allow a high expression level of the foreign gene and a targeted control of the expression. The promoters P1 and P2 were newly developed by the inventors. The remaining promoters originate from the vaccinia virus and are described in other connections in Davidson and Moss (1989), Structure of Vaccinia virus late promoters, J. Mol. Biol., Vol. 210, pages 771 to 784, and Yang et al. (2011), Genome-wide analysis of the 5' and 3' ends of Vaccinia Virus early mRNAs delineates regulatory sequences of annotated and anomalous transcripts, J. Virology, Vol. 85, Nr. 12, S. 5897-5909, Broyles (2003), Vaccinia virus transcription, J. gene. Virol., Vol. 84, Nr. 9, S. 2293-2303. According to the findings of the inventors P2 causes a significantly increased expression strength in comparison to P1. This was surprising because the promoter P1 corresponds by 100% to the consensus sequence from the Vaccinia virus, however not P2. The low expression of the "optimum" Vaccinia-virus promoter (Orthopox) in ORFV (parapox) is a contradiction and surprising. It is also surprising that the P2 promoter results in a strong expression.

According to a further embodiment of the recombinant ORFV vector according to the invention the promoter is located at a position of nt 28±10 to nt-13±10 upstream in relation to the nucleotide sequence encoding for the foreign gene.

This measure has the advantage that the promoter is localized at such a position which allows a high expression strength and a controlled expression of the foreign gene.

According to a further embodiment of the recombinant ORFV vector according to the invention at least in one of the IL 1, 2 or 3 there is inserted more than one, preferably 2, 3, 4 or more nucleotide nucleotide sequences encoding and expression a foreign gene.

This measure has the advantage that by means of one recombinant ORFV vector according to the invention multiple foreign genes can be expressed. This embodiment is especially appropriate for the production of polyvalent vaccines which, at the same time, are directed against a number of antigenic structures. In every insertion locus multiple foreign genes, preferably 2, 3, 4 or more, can be expressed.

In a configuration which is preferred according to the invention the recombinant ORFV vector comprises an additional nucleotide sequence encoding and expressing a foreign gene, which is under the control of preferably an early ORFV promoter, and is inserted into an insertion locus which in the ORFV genome is located in the vegf E gene.

This measure has the advantage that an insertion locus is employed which is already described and well characterized in the prior art. The use of the vegf locus can be used for a targeted control of the gene expression. In the vegf locus the expression of a foreign gene can be increased in comparison to any of the new expression loci, e.g. IL 2.

According to an embodiment which is preferred according to the invention the foreign gene of the recombinant ORFV vector is selected from the group of the following antigens:

viral antigen, preferably
rabies virus antigen, including glycoprotein (RabG);
influenza A antigen, including nucleoprotein (NP), hemagglutinin (HA), neuraminidase (NA);
tumor antigen, preferably viral tumor antigen, including HPV selective viral tumor antigen;
tumor associated antigen, including viral tumor associated antigen, including HPV-selective viral tumor associated antigen;
parasitic antigen, preferably plasmodium antigen;
cytokine.

This measure has the advantage that especially important antigens, in particular for the production of vaccines, are expressible via the recombinant ORFV virus according to the invention.

Another subject matter of the present invention relates to a biological cell, preferably a mammalian cell, further preferably a Vero cell, containing the ORFV vector according to the invention.

Another subject matter of the present invention relates to a composition, preferably a pharmaceutical composition, containing the ORFV vector of the invention and/or the cell of the invention. The pharmaceutical composition can be preferably a vaccine, further preferably a polyvalent vaccine.

The characteristics, advantages, features, and further developments of the ORFV vector according to the invention apply to the cell of the invention and the composition of the invention in a corresponding manner.

Another subject matter of the present invention relates to the use of the recombinant ORFV vector according to the invention for the expression of at least one foreign gene, further preferably for the expression of at least one vaccine containing one foreign gene product (monovalent vaccine), further preferably of a vaccine containing at least two foreign gene products (polyvalent vaccine).

In this context "at least" means that 2, 3, 4, 5, 6, 7, 8, 9 etc. foreign genes are encompassed.

The features, advantages, characteristics and further developments of the recombinant ORFV vector according to the invention apply to the use of the invention in a corresponding manner.

Another subject matter of the present invention relates to a nucleic acid molecule encoding an ORFV promoter, preferably an early ORFV promoter comprising a nucleotide sequence which is selected from the nucleotide sequences SEQ-ID No. 1 (P1) and SEQ-ID No. 2 (P2).

The nucleic acid molecule according to the invention encodes new ORFV promoters which are especially suited for the expression of foreign genes in the recombinant ORFV vector. The promoters cause a very strong early gene expression.

It is to be understood that the previously mentioned features and those to be explained in the following cannot only be used in the combination indicated in each case, but also in other combinations or in isolated position without departing from the scope of the invention.

The invention is now further explained by means of examples which result in additional features, advantages and characteristics of the invention. The examples are purely illustrative and do not restrict the scope of the invention. Reference is made to the enclosed figures.

EXAMPLES

1. The ORFV genome

The ORFV genome consists of a linear double-stranded DNA and has a length of about 138 kB, a GC content of about 64% and comprises 130-132 genes. The construction of the ORFV genome is similar to that of other pox viruses. It consists of a central region with essential genes which comprise a high degree of conservation within the pox viridae. In the ORFV genome there are 88 genes which are conserved in all Chordopoxvirinae. In the terminal regions viral genes are localized which are non-essential for the growth in vitro, however which are relevant for the pathogenicity and the tropism of the virus.

Figure 1:
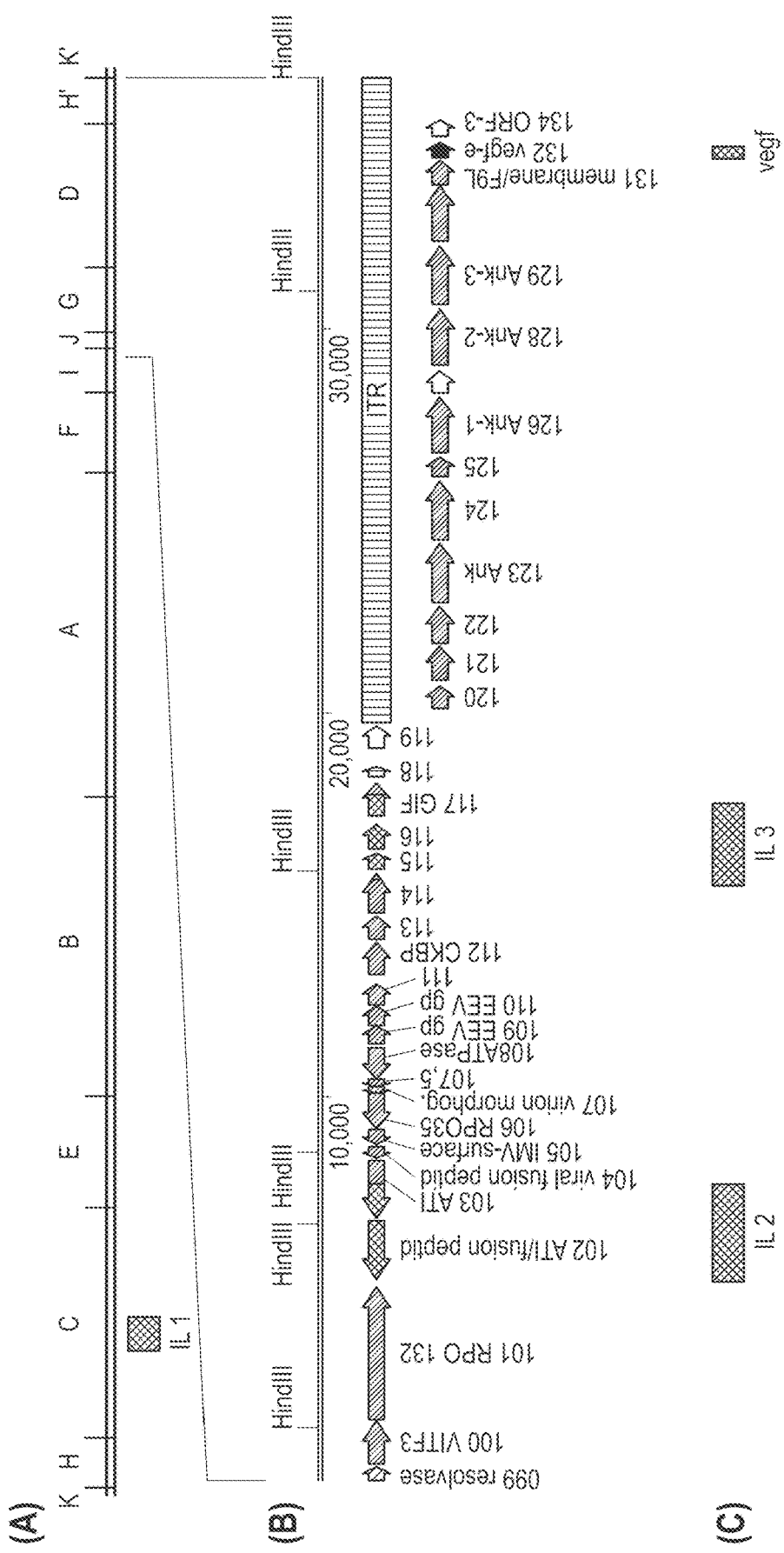
FIG. 1 shows the map of the Hind III restriction fragments of the ORFV D1701-V DNA genome. The hatched boxes represent the insertion positions IL1, IL2, IL3 and vegf. ITRL stands for the inverted terminal repeats of the ends of the genome.

In comparison to other Orf viruses the D1701 virus which is adapted to the replication in cell culture shows a significant enlargement of the inverted terminal repeats (ITR). These alterations do not only cause a loss but also a duplication of several genes, including the vegf-e gene. The adaptation of D1701-B amplified in bovine BKKL3A cells to the growth in Vero cells resulted in three additional insertion loci IL 1, IL 2 and IL 3 in the virus genome which is now referred to as D1701-V. They are illustrated in the FIG. 1.

2. Poxvirus Promoters

Poxviruses comprise "early", "intermediate" and "late" promoters. These different promoters comprise several characteristic sequence features, which is further explained in the following with the example of VACV. The "early" promoter of the VACV consists of a critical region with the length of 16 or 15 nucleotides, respectively, which are spaced by an initiator region with a length of 7 nucleotides by a spacer region of 11 nucleotides. This critical region is rather adenine rich, whereas the spacer region is rather rich in thymine. The initiation of the transcription always takes place at a purine, with rare exceptions. Nucleotide substitutions in the critical region may have a dramatically negative effect on the promoter activity, even a complete loss of the activity is possible. Substitution analysis of the early VACV 7.5 kDa promoter showed an optimized critical region, in addition it was succeeded in deriving a consensus sequence for the "early" poxvirus promoter which is shown in the table 1. The "intermediate" promoters consist of an AT rich core sequence which is about 14 nucleotides long, followed by a spacer region of 10-11 nucleotides, which is followed by a short initiator region. The structure of the "late" promoters consists of an upstream AT-rich region of about 20 nucleotides which is separated from the transcription start position by a spacer region of about 6 nucleotides which includes the highly conserved sequence-1 TAAAT+4.

TABLE 1

Used promoters; P1 and P2 were newly developed by the inventors.

| | critical region | | | | | | | | | | |
|---|---|---|---|---|---|---|---|---|---|---|---|
| | −28 | −27 | −26 | −25 | −24 | −23 | −22 | −21 | −20 | −19 | −18 |
| optimized "early" | A | A | A | A | A | T | T | G | A | A | A |
| 7.5 kDa promoter | A | A | A | A | G | T | A | G | A | A | A |
| consensus "early" | A | A | A | A | A | A | T | G | A | A | A |
| VEGF | C | A | A | A | A | T | G | T | A | A | A |
| P1 | A | A | A | A | A | T | T | G | A | A | A |
| P2 | A | A | A | A | A | T | T | G | A | A | A |

| | critical region | | | | | SEQ ID | % identity with opt. "early" | | |
|---|---|---|---|---|---|---|---|---|---|
| | −17 | −16 | −15 | −14 | −13 | | | | |
| optimized "early" | A | A | C/T | T | A | 3 | | Spacer region | Initiator Region |
| 7.5 kDa promoter | A | T | | T | A | 4 | 75 | Thymine rich −12 to −2 | Start mostly at purine-1 to 6 |
| consensus "early" | A | A | A | A/T | A | 5 | 87.5 | | |
| VEGF | T | T | A | T | A | 6 | 62.5 | | |
| P1 | A | A | T | T | A | 1 | 100 | | |
| P2 | T | T | C | T | A | 2 | 87.5 | | |

3. Production of the Recombinant ORFV Vector

The inventors have searched for a new strategy for the production of a recombinant polyvalent ORFV vector. During the adaption of ORFV to Vero culture cells several deletions in the viral genome have occurred. It was examined whether the regions of the deletions are suited for the integration of foreign genes (FIG. 1A).

Figure 2:
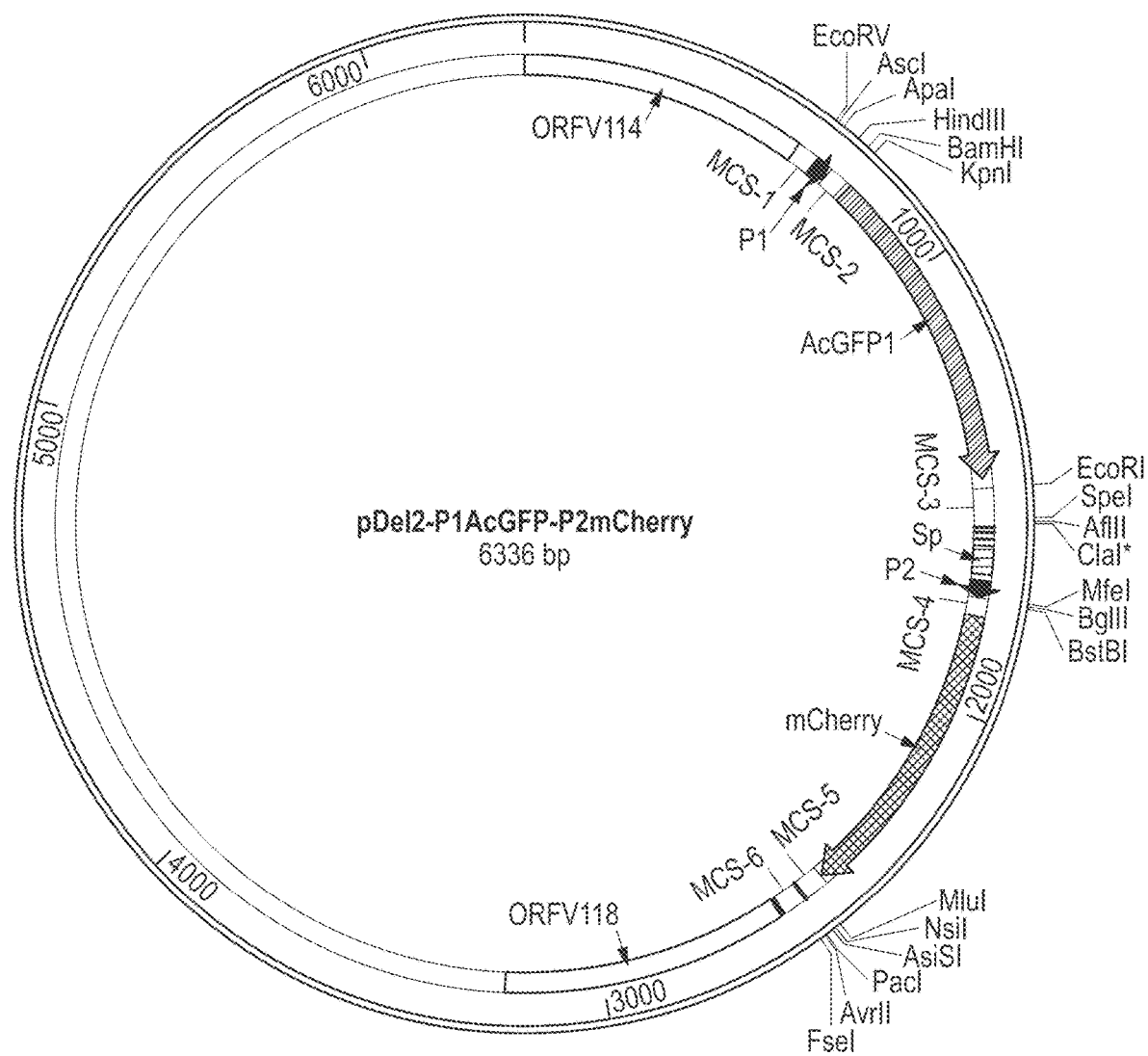
FIG. 2 shows a schematic representation of the transfer plasmid pD1-GFP-D2Cherry. The vector shows the AcGFP gene (line hatching) which stands under the control of the artificial early promoter P1 (black arrow, top), and the mCherry gene (box hatching) which stands under the control of the artificial early promoter P2 (black arrow, right). Following both fluorescence genes there are pox-virus specific early transcription stop motives T5NT (black). The genes are separated from each other via a spacer (Sp). Several multiple cloning sites (MCS 1-6) allow the exchange of the fluorescence marker gene by the desired foreign genes. The genes enclose flanking regions which are downstream homologous to the ORFV genome region ORF117/118, upstream homologous to the ORFV genome region ORF114, and allow a targeted integration into the IL 2 locus of the D1701-V genome via homologous recombination.

For this reason, along with further plasmids the transfer plasmid pDel2 was designed which includes the homologous sections of the IL 2 region (FIG. 2). The cloning of foreign genes into the plasmid was enabled by using several MCS (multiple cloning sites). Additionally, the plasmid was designed in such a way that it allows the simultaneous integration of multiple foreign genes which are each under the control of artificial early ORFV promoters and which are bounded by pox-virus specific T5NT early transcription stop motives (FIG. 2).

Nucleotide sequences of the new artificial early ORFV promoters P1 and P2 were designed.

In a first experiment it should be examined whether the IL 2 locus is appropriate for the stabile integration of foreign genes. For this purpose the mCherry fluorescence marker gene was cloned under the control of the promoter P2 into the pDel2 transfer plasmid. In the following the plasmid was transfected into Vero cells which were infected by D1701-VrV, and new recombinant viruses were visually selected after the identification of red-shiny cells by means of fluorescence microscopy and the homogenous recombinant D1701-V-D2-Cherry obtained via several plaque purifications was cultivated (FIG. 3A,a).

Figure 3:
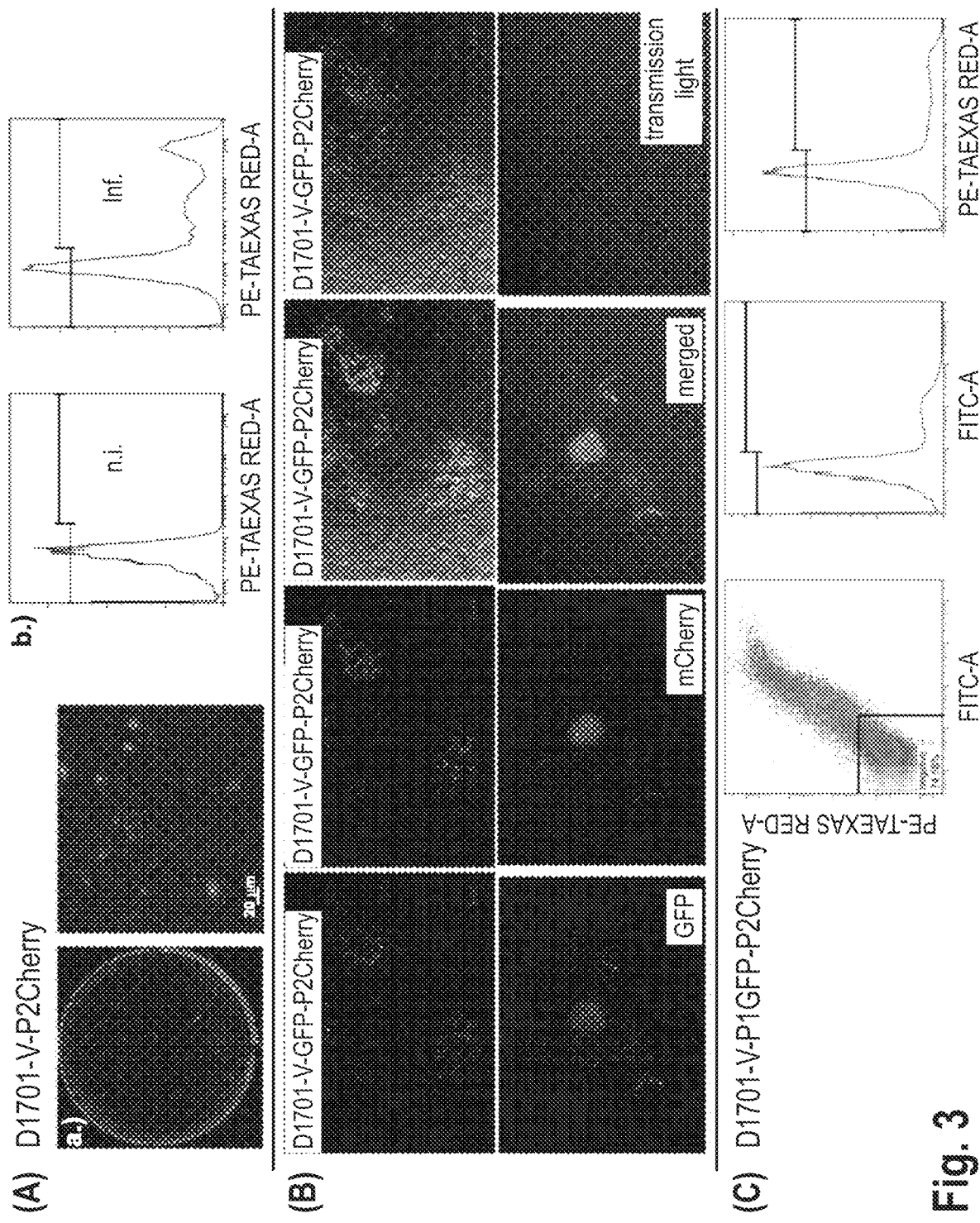
FIG. 3 shows an expression analysis of different fluorescence recombinants. (A,a) Fluorescence microscopic image of a 6-well plate with D1701-V-D2Cherry infected Vero cells. For the selection of the recombinants Cherry fluorescent plaques were picked and the virus was grown from the plaques. After four plaque purifications the homogenity of D1701-V-D2Cherry was ensured via PCR analyses. (A,b) Determination of the Cherry expression by means of flow cytometry. The figure shows exemplarily the expression of D1701-V-D2Cherry infected Vero cells (MOI=1.0) in the flow cytometer. After 48 hours approx. 45% of all living single cells express Cherry. Non-infected Vero cells serve as negative control. (B) Fluorescence expression of the recombinant D1701-VGFP-D2Cherry Vero cells were infected with D1701-V-GFP-D2Cherry (MOI=0.5). In the top row a fluorescence image 48 hours after the infection is shown (magnification: 20×). The lower row shows the fluorescence expression after 24 hours (magnification: 63×). The fluorescence microscopy allows the imaging of the AcGFP-(GFP), the mCherry expression (mCherry), and of both fluorescences in one cell (merged). In addition, the cells were imaged in the microscope transmitted light (transmitted light). (C) Fluorescence expression of the recombinant D1701-V-D1GFP-D2Cherry. Vero cells were infected with D1701-V-D1GFP-P2Cherry (MOI=1.0) and the expression was determined in the flow cytometer. After 24 hours approx. 25% of all living single cells express both mCherry and also GFP. Non-infected Vero cells were used as negative control.

The correct integration of the mCherry gene into the IL 2 locus of D1701-VrV was ensured by specific PCR analyses and Southern blot hybridizations, the correct expression could be demonstrated by fluorescence and Western blot analyses but also by means of flow cytometry (FIG. 3A,b).

In this context a strong expression could be detected early after the infection. By multiple passages in vitro of the recombinant it could be demonstrated that the integration of the foreign gene into the ORFV genome was stable.

It could be also demonstrated by means of the generated recombinant D1701-V-GFP-D2-Cherry where the AcGFP gene is integrated in the vegf-e gene and the mCherry gene is integrated into the IL 2 locus that two fluorescence genes were simultaneously early expressed in different insertion loci (FIG. 3B).

Furthermore it should be examined whether at the same time a second foreign gene can be stably integrated into the IL 2 locus. For this purpose, in addition to the P2-controlled mCherry gene the AcGFP gene under the control of the P1 promoter was cloned into the pDel2 transfer plasmid. The selection and purification of the homologous recombinant D1701-V-D1-GFP-D2-Cherry was realized in analogy to the previously described D1701-V-P2-Cherry selection.

Again, the correct integration of both of the foreign genes into the IL 2 locus was demonstrated via PCR and Southern blot analysis. The detection of the expression was made via fluorescence microscopy and flow cytometry (FIG. 3C).

Figure 4:
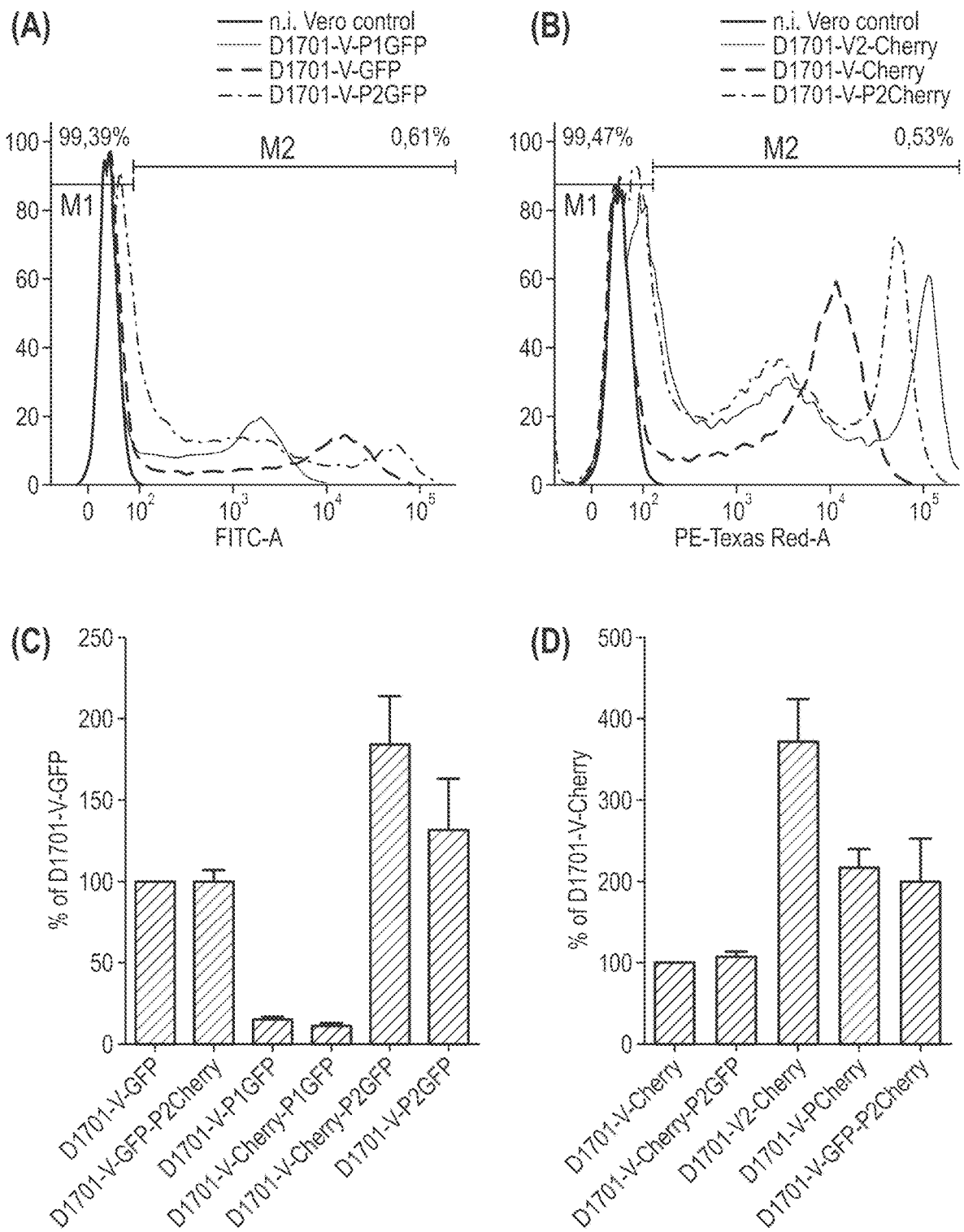
FIG. 4 shows the determination of the fluorescence intensities of the various recombinants. (A) Vero cells were infected with GFP expressing recombinants (MOI approx. 1.5) and 24 hours later the average fluorescence intensity was determined by flow cytometer. Non-infected Vero cells serve as negative control. M1 describes the region where 99.39% of all non-infected cells (front first curve) can be detected. In contrast, in the region M2 the GFP-positive cells can be found. The population of GFP-positive cells after the infection was comparable with the GFP-expressing recombinants (38.2%-40.0%). It was apparent that the GFP intensity in D1701-V-D1GFP-infected cells (continuous line) was the lowest, in D1701-V-D2GFP-infected cells (•-•-•-•-) was the strongest. (B) Vero cells were infected with mCherry-expressing recombinants (MOI approx. 3.0) and 24 hours later the average fluorescence intensity was measured by flow cytometry. Non-infected Vero cells serve as negative control. M1 describes the area where 99.47% of all non-infected cells (front first curve) can be detected. In contrast, in the area M2 there are Cherry-positive cells. The population of mCherry-positive cells after the infection was comparable with the GFP-expressing recombinants (62.5%-63.3%). The mCherry intensity in D1701-V-Cherry-infected cells (- - - - -) was significantly lower than in D1701-V-D2Cherry (blue line) or in D1701-V2Cherry-infected cells (red line). (C+D) The graphs show the percentage of the fluorescence intensity of various fluorescence recombinants in relation to D1701-V-GFP (C) or to D1701-V-Cherry (D). The data represent mean values from at least 3 independent experiments.

The strength of the promoter P1 and P2 was compared among each other and with the promoter $P_{vegf}$ in expression analyses. It could be shown that the promoter P2 induced the strongest and the promoter P1 included the weakest gene expression (FIG. 4A+4C). This was surprising because P1 corresponds by 100% to the consensus sequence from the vaccinia virus, not P2.

It could also be demonstrated that the integration of a second regulated foreign gene under the control of an individual promoter has no effect on the expression strength of the first foreign gene. It was irrelevant whether the second gene was integrated into the same or a different insertion locus. After the insertion of a P2-controlled mCherry gene into the VEGF locus the influence of the insertion region could be analyzed in comparison with the recombinant which had the P2-regulated mCherry gene integrated into the IL 2 locus. It could be shown that the gene expression in the VEGF locus was about two times stronger than in the IL 2 locus (FIG. 4B+4D).

To summarize, it could be shown that the Orf virus vector D1701-V is very well suited for the production of polyvalent recombinants. Several foreign genes could be stably integrated into the viral genome, e.g. via the newly discovered insertion loci IL 1, 2 and 3, or via the known insertion locus VEGF. The strength of the foreign gene expression depends both on the promoter but also on the insertion locus. The strongest gene expression was achieved after the integration of a P2-controlled foreign gene into the VEGF locus.

The inventors have generated further various vectors which can be distinguished from the kind and constellation of the different marker foreign genes, insertion regions and promoters (Tab. 2).

TABLE 2

Tabular overview on the newly generated fluorescent ORFV vectors.

| Recombinant | Locus VEGF | Locus IL2 | Foreign Gene Expression |
|---|---|---|---|
| D1701-V-Cherry | $P_{vegf}$: mCherry | — | +++ |
| D1701-V-Cherry-D1GFP | $P_{vegf}$: mCherry | P1: AcGFP | +++/+ |
| D1701-V-Cherry-D2GFP | $P_{vegf}$: mCherry | P2: AcGFP | +++/++++ |
| D1701-V12-Cherry | P2: mCherry | — | ++++ |
| D1701-V12-Cherry-D2GFP | P2: mCherry | P2: AcGFP | ++++/++++ |
| D1701-V-GFP | $P_{vegf}$: AcGFP | — | +++ |
| D1701-V-GFP-D2Cherry | $P_{vegf}$: AcGFP | P2: mCherry | +++/++++ |
| D1701-V-GFP-D2CD4 | $P_{vegf}$: AcGFP | P2: hCD4 | +++/++++ |
| D1701-V-D1GFP | $P_{vegf}$: LacZ | P1: AcGFP | +++/+ |
| D1701-V-D1GFP-D2Cherry | $P_{vegf}$: LacZ | P1: AcGFP, P2: mCherry | +++/+/++++ |
| D1701-V-D2GFP | $P_{vegf}$: LacZ | P2: AcGFP | +++/++++ |
| D1701-V-D2Cherry | $P_{vegf}$: LacZ | P2: mCherry | +++/++++ |
| D1701-V-D2Orange | $P_{vegf}$: LacZ | P2: mOrange | +++/++++ |
| D1701-V-CD4-D2Cherry | $P_{vegf}$: hCD4 | P2: mCherry | +++/++++ |

The table gives an overview on the fluorescent recombinant ORFV vectors which were generated during the works resulting in the invention. The region of insertion (locus) and the promoters used for controlling the foreign gene expression ($P_{vegf}$, P1, P2) are indicated in the table for each of the recombinants. In addition, the strength of the foreign gene expression is indicated (very strong=++++ to weak=+).

The invention creates a variety of options for the development of new recombinant ORFV based vaccines. Recombinants can be generated which simultaneously express multiple antigens. This could be a significant advantage in the production of a universal vaccine of combination vaccines or of therapeutic tumor vaccines which are directed against multiple tumor antigens. In addition, the immune response can be influenced by a simultaneous insertion of antigene and cytokines in a targeted manner.

What is claimed is:

1. A recombinant Orf virus (ORFV) vector, which comprises:
   (1) at least one nucleotide sequence encoding and expressing a foreign gene, and
   (2) at least one promoter controlling the expression of the nucleotide sequence, wherein:
   the nucleotide sequence is localized in at least one of insertion loci (IL) 1, 2 and 3, which are localized in the ORFV genome in a region selected from the group consisting of the following regions:

|  | IL 1 | IL 2 | IL 3 |
   | --- | --- | --- | --- |
   | Restriction fragment | HindIII fragment C, KpnI fragment G, BamHI fragment C/G, EcoRI fragment B | HindIII fragment I/J, KpnI fragment B, BamHI fragment A, EcoRI fragment A/E | HindIII fragment G/D, KpnI fragment B, BamHI fragment A, EcoRI fragment D |
   | Gene/ORF and | 006, 007 (dUTPase), 008 (G1L-Ank), 009 (G2L) | 102, 103 | 114, 115, 116, 117 (GIF) |
   | Nucleotide position | nt 500 ± 100 to nt 2,400 ± 600 | nt 5,210 ± 100 to nt 7,730 ± 100 | nt 15,660 ± 100 to nt 17,850 ± 100, | and wherein the OFFV is of the strain D1701.

2. The recombinant ORFV vector of claim 1, wherein the at least one ORFV promoter is an early ORF promoter.

3. The recombinant ORFV vector of claim 2, wherein the early ORF promoter comprises a nucleotide sequence which is selected from the group consisting of: SEQ ID No. 1 (P1), SEQ ID No. 2 (P2), SEQ ID No. 3 ("optimized early"), SEQ ID No. 4 (7.5 kD promoter), and SEQ ID No. 5 (VEGF).

4. The recombinant ORFV vector of claim 1, wherein the at least one promoter is located at a position of nt 28±10 to nt-13±10 upstream in relation to the nucleotide sequence encoding the foreign gene.

5. The recombinant ORFV vector of claim 1, wherein at least in one of the IL 1, 2 or 3 there is inserted more than one nucleotide sequence encoding and expressing a foreign gene.

6. The recombinant ORFV vector of claim 5, wherein the number of the inserted nucleotide sequences encoding and expressing a foreign gene is selected from the group consisting of: 2, 3, 4 and more than 4.

7. The recombinant ORFV vector of claim 1, further comprising an additional nucleotide sequence encoding and expressing a foreign gene, which is under the control of an early ORFV promoter, and is inserted into an insertion locus which in the ORFV genome is located in the vegf E gene.

8. The recombinant ORFV vector of claim 1, wherein the foreign gene is selected from the group consisting of the following antigens:
   a viral antigen;
   a tumor antigen;
   a tumor associated antigen;
   a parasitic antigen; and
   a cytokine.

9. A cell containing the recombinant ORFV vector of claim 1.

10. The cell of claim 9, which is a mammalian cell.

11. The cell of claim 9, which is a Vero cell.

12. A pharmaceutical composition containing the recombinant ORFV vector of claim 1.

13. The pharmaceutical composition of claim 12, which is a vaccine.

14. A pharmaceutical composition containing the cell of claim 9.

15. The pharmaceutical composition of claim 14, which is a vaccine.

16. The recombinant ORFV vector of claim 8, wherein the viral antigen is:
   a rabies virus antigen; or
   an influenza A antigen selected from the group consisting of nucleoprotein (NP), hemagglutinin (HA) and neuraminidase (NA).

17. The recombinant ORFV vector of claim 8, wherein the tumor antigen is a viral tumor associated antigen.

18. The recombinant ORFV vector of claim 8, wherein the viral tumor associated antigen is HPV selective viral tumor-associated antigen.

19. The recombinant ORFV vector of claim 8, wherein the parasitic antigen is plasmodium antigen.

* * * * *

UNITED STATES PATENT AND TRADEMARK OFFICE
CERTIFICATE OF CORRECTION

PATENT NO. : 11,286,500 B2
APPLICATION NO. : 15/875389
DATED : March 29, 2022
INVENTOR(S) : Hanns-Joachim Rziha It is certified that error appears in the above-identified patent and that said Letters Patent is hereby corrected as shown below:

In the Specification

Column 2, Line 59-60 (approx.), delete "interferones," and insert --interferons,--.

Column 3-4, Line 30 (approx.), delete "Nucleotid" and insert --Nucleotide--.

Column 7, Line 49, delete "ITRL" and insert --ITR--.

Column 8, Line 6 (approx.), delete "homogenity" and insert --homogeneity--.

Column 12, Line 7, delete "could shown" and insert --could be shown--.

Column 12, Line 61 (approx.), delete "antigenes." and insert --antigens.--.

Column 12, Line 67 (approx.), delete "antigene" and insert --antigen--.

Column 13-14, Line 50, delete "attawa" and insert --attata--.

In the Claims

Column 15, Line 21 (approx.), Claim 1, below "EcoRI fragment B" insert --and/or--.

Column 15, Line 24 (approx.), Claim 1, delete "and" and insert --and/or--.

Column 15, Line 27 (approx.), Claim 1, delete "OFFV" and insert --ORFV--.

Column 15, Line 38 (approx.), Claim 4, delete "nt-13±10" and insert --nt 13±10--.

Signed and Sealed this
Thirteenth Day of September, 2022

Katherine Kelly Vidal
*Director of the United States Patent and Trademark Office*

SEQUENCE LISTING

<160> NUMBER OF SEQ ID NOS: 5

<210> SEQ ID NO 1
<211> LENGTH: 16
<212> TYPE: DNA
<213> ORGANISM: Artificial Sequence
<220> FEATURE:
<223> OTHER INFORMATION: P1 Promoter

<400> SEQUENCE: 1
aaaaattgaa aaatta                                                 16

<210> SEQ ID NO 2
<211> LENGTH: 16
<212> TYPE: DNA
<213> ORGANISM: Artificial Sequence
<220> FEATURE:
<223> OTHER INFORMATION: P2 Promoter

<400> SEQUENCE: 2
aaaaattgaa attcta                                                 16

<210> SEQ ID NO 3
<211> LENGTH: 16
<212> TYPE: DNA
<213> ORGANISM: Artificial Sequence
<220> FEATURE:
<223> OTHER INFORMATION: optimized early Promoter
<220> FEATURE:
<221> NAME/KEY: variation
<222> LOCATION: (14)..(14)
<223> OTHER INFORMATION: y is t or c

<400> SEQUENCE: 3
aaaaattgaa aaayta                                                 16

<210> SEQ ID NO 4
<211> LENGTH: 15
<212> TYPE: DNA
<213> ORGANISM: Artificial Sequence
<220> FEATURE:
<223> OTHER INFORMATION: 7.5 kDa Promoter

<400> SEQUENCE: 4
aaaagtagaa aatta                                                  15

<210> SEQ ID NO 5
<211> LENGTH: 16
<212> TYPE: DNA
<213> ORGANISM: Artificial Sequence
<220> FEATURE:
<223> OTHER INFORMATION: consensus early promoter
<220> FEATURE:
<221> NAME/KEY: variation
<222> LOCATION: (15)..(15)
<223> OTHER INFORMATION: w is a or t

<400> SEQUENCE: 5
caaaatgtaa attawa                                                 16